United States Patent [19]

Hoshino

[11] Patent Number: 5,491,005

[45] Date of Patent: Feb. 13, 1996

[54] GOLD THIN FILM VAPOR GROWING METHOD

[75] Inventor: Masataka Hoshino, Kawasaki, Japan

[73] Assignee: Fujitsu Limited, Kawasaki, Japan

[21] Appl. No.: 317,838

[22] Filed: Oct. 4, 1994

Related U.S. Application Data

[63] Continuation of Ser. No. 17,255, Feb. 12, 1993, abandoned.

[30] Foreign Application Priority Data

May 25, 1992 [JP] Japan ................................. 4-156159
Nov. 13, 1992 [JP] Japan ................................. 4-303751
Jan. 26, 1993 [JP] Japan ................................. 5-028454

[51] Int. Cl.$^6$ ........................... H05H 1/24; C23C 16/00; C30B 29/52
[52] U.S. Cl. .................. 427/576; 427/250; 427/255.7; 427/124; 427/125; 427/271; 117/103; 117/938
[58] Field of Search ................. 427/250, 255.7, 427/576, 569, 124, 125, 271; 156/610, 613, DIG. 101; 117/938, 103

[56] References Cited

U.S. PATENT DOCUMENTS

| | | | |
|---|---|---|---|
| 4,714,627 | 12/1987 | Puddephatt et al. | 427/125 |
| 4,888,204 | 12/1989 | Tutt et al. | 427/584 |
| 5,019,531 | 5/1991 | Awaya et al. | 427/125 |

FOREIGN PATENT DOCUMENTS

| | | |
|---|---|---|
| 9002827 | 3/1990 | European Pat. Off. . |
| 0451502 | 10/1991 | European Pat. Off. . |
| 3916622 | 11/1989 | Netherlands . |

OTHER PUBLICATIONS

Holloway et al., "Morphology and Deposition Conditions of CVD Au Films", *Mat. Res. Syp Proc.*, vol. 204, 1991, US pp. 409–414.

"Thin Film Forming Device", *Patent Abstracts of Japan*, vol. 9, No. 66, Mar. 26, 1985.

"Multilayered Reflecting Mirror for X–Ray Optic", *Patent Abstracts of Japan*, vol. 15, No. 384, Sep. 27, 1991.

*Primary Examiner*—Roy V. King
*Attorney, Agent, or Firm*—Staas & Halsey

[57] ABSTRACT

A method of growing, in a vapor phase, a gold film having high electro-migration resistance and a flat surface, and capable of being buried in contact holes disposed in an insulating film of an integrated circuit device, for example, at a practical growing rate. Dimethylgold hexafluoroacetylacetonato (DMAu(hfac)), for example, is used as a starting gas, and vapor growth is carried out under specific conditions by utilizing thermal CVD. Adhesion of the gold film can be improved by converting it to a two-layered film by the combination of plasma enhanced CVD with thermal CVD.

15 Claims, 19 Drawing Sheets

I. REACTION RATE DETERMINING RANGE

Fig. 4(A) LOW PRESSURE (1.5 Torrs) DMAu(hfac) REACHES SUBSTATE UNDECOMPOSED AND MIGRATES OVER LONG DISTANCE

NUCLEUS FORMATION DENSITY: SMALL

Fig. 4(B) HIGH PRESSURE (30 Torrs OR ABOVE) DMAu(hfac) IS LIGHTLY DECOMPOSED IN VAPOR PHASE, REACHES SUBSTRATE AND MIGRATES OVER MEDIUM DISTANCE

NUCLEUS FORMATION DENSITY: GREAT

II. TRANSPORT RATE DETERMINING RANGE

Fig. 4(C) LOW PRESSURE (1.5 Torrs) DMAu(hfac) REACHES SUBSTRATE UNDECOMPOSED AND MIGRATES OVER SHORT DISTANCE

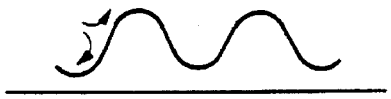

DECOMPOSES WHILE SELECTING SITE

Fig. 5(A)
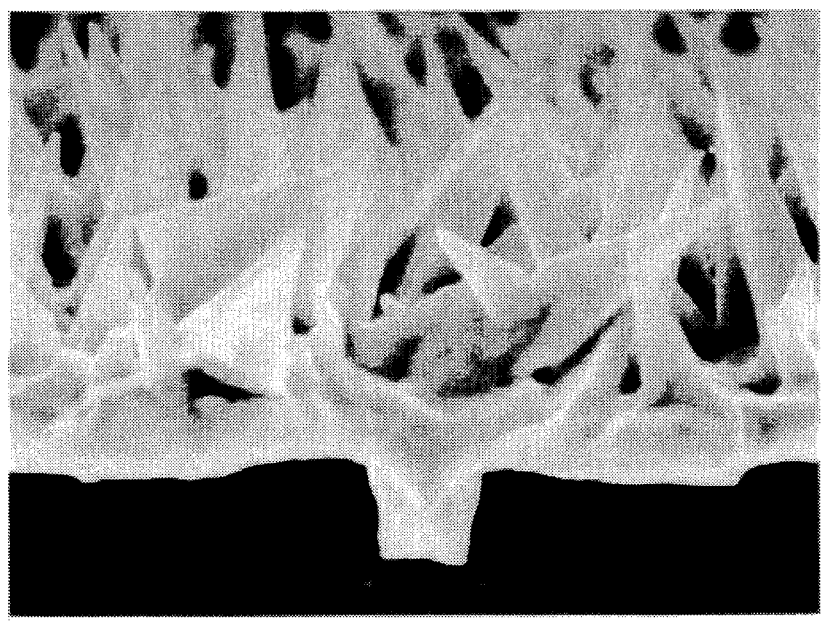
240°C  1.5Torr
Fig. 5(B)
240°C  10Torr
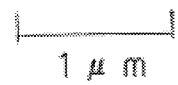
1 μm 240°C   50Torr

GOLD THIN FILM VAPOR GROWING METHOD

This application is a continuation of U.S. application Ser. No. 08/017,255, filed Feb. 12, 1993, now abandoned.

BACKGROUND OF THE INVENTION

1. Field of the Invention

This invention relates to a vapor growing method of a gold (Au) thin film, particularly a gold thin film having a flat surface, on a substrate.

2. Description of the Related Art

A thin film of aluminum (Al), etc., has been used primarily as a material of a wiring layer of an LSI, and the like.

However, when the aluminum thin film is used as the material of a wiring layer, electromigration and corrosion are likely to occur, so that degradation of the characteristics of LSIs, etc., and the reduction of the service life of these devices occur.

To eliminate these problems, the use of gold, which is highly resistant to electromigration and corrosion and can ensure high reliability for an extended period of time even in a corrosive environment, as the wiring layer material has been considered.

To obtain a thin film single crystal it has been possible conventionally to grow the thin film using a molecular beam epitaxy method, a cluster ion beam method and a gas temperature control method. However, step coverage necessary for LSI wirings has been difficult to attain using the first two of these methods, and up until now a report has only been made on the Al growth using the gas temperature control method. Therefore, a gold wiring layer by CVD (Chemical Vapor Deposition), having excellent step coverage properties, is preferable, but it has not been possible to form a flat thin film except by thermal excitation CVD of Al.

When about 1 μm-thick gold thin film is formed at a practical growing rate of 10 μm/hr using the conventional CVD process, a needle-like crystal grows on the surface of the thin film. It has therefore been extremely difficult to obtain a gold thin film having a thickness sufficient to serve as a wiring layer and a flat surface at such a practical growing rate.

SUMMARY OF THE INVENTION

In view of the problems with the prior art described above, the present invention aims at providing a method of growing a flat gold film at a practical growing rate without involving the growth of a needle-like crystal. The present invention also aims at obtaining a gold thin film having sufficient resistance to electromigration.

The present invention is further directed to provide a method of growing a gold thin film having good step coverage and a flat single crystal by a plasma enhanced chemical vapor deposition (hereinafter referred to as "plasma enhanced CVD"), and to further improve electromigration resistance by the formation of a single crystal thin film.

The above and other objects and novel features of the present invention will become more apparent from the following detailed description, when taken in conjunction with the accompanying drawings.

BRIEF DESCRIPTION OF THE ACCOMPANYING DRAWINGS

Figure 6:
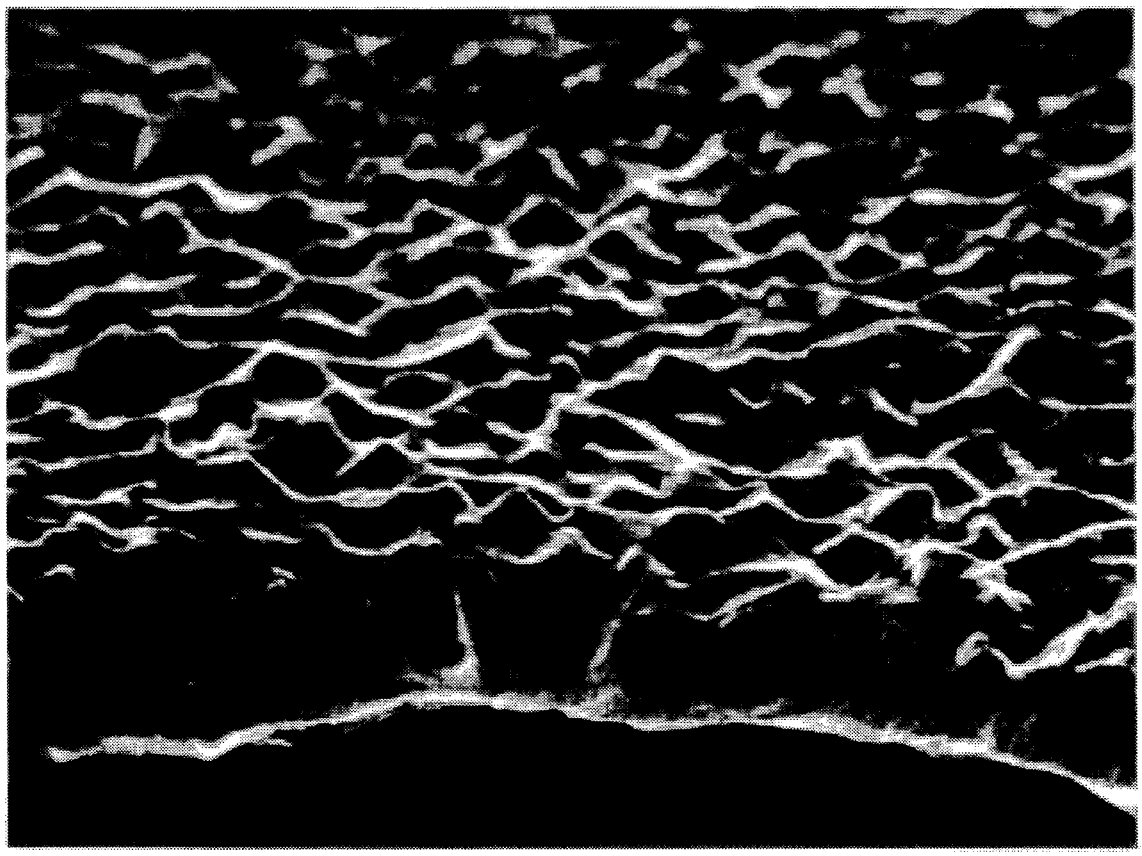
Figure 7:
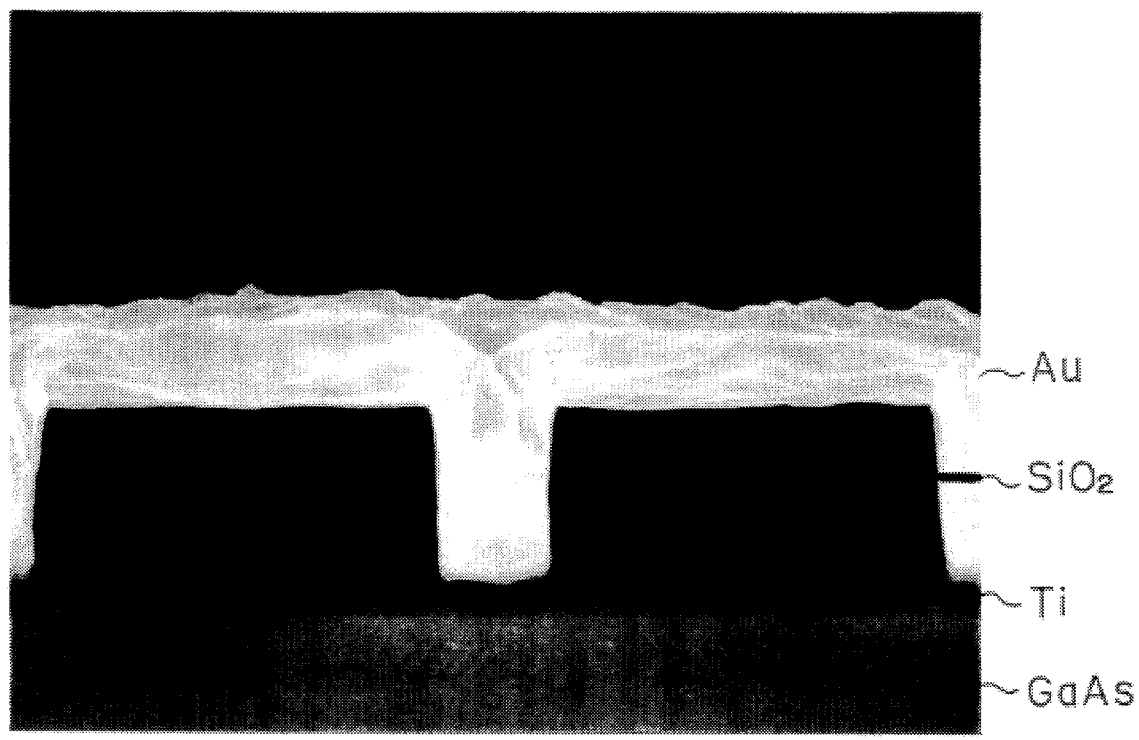
Figure 8:
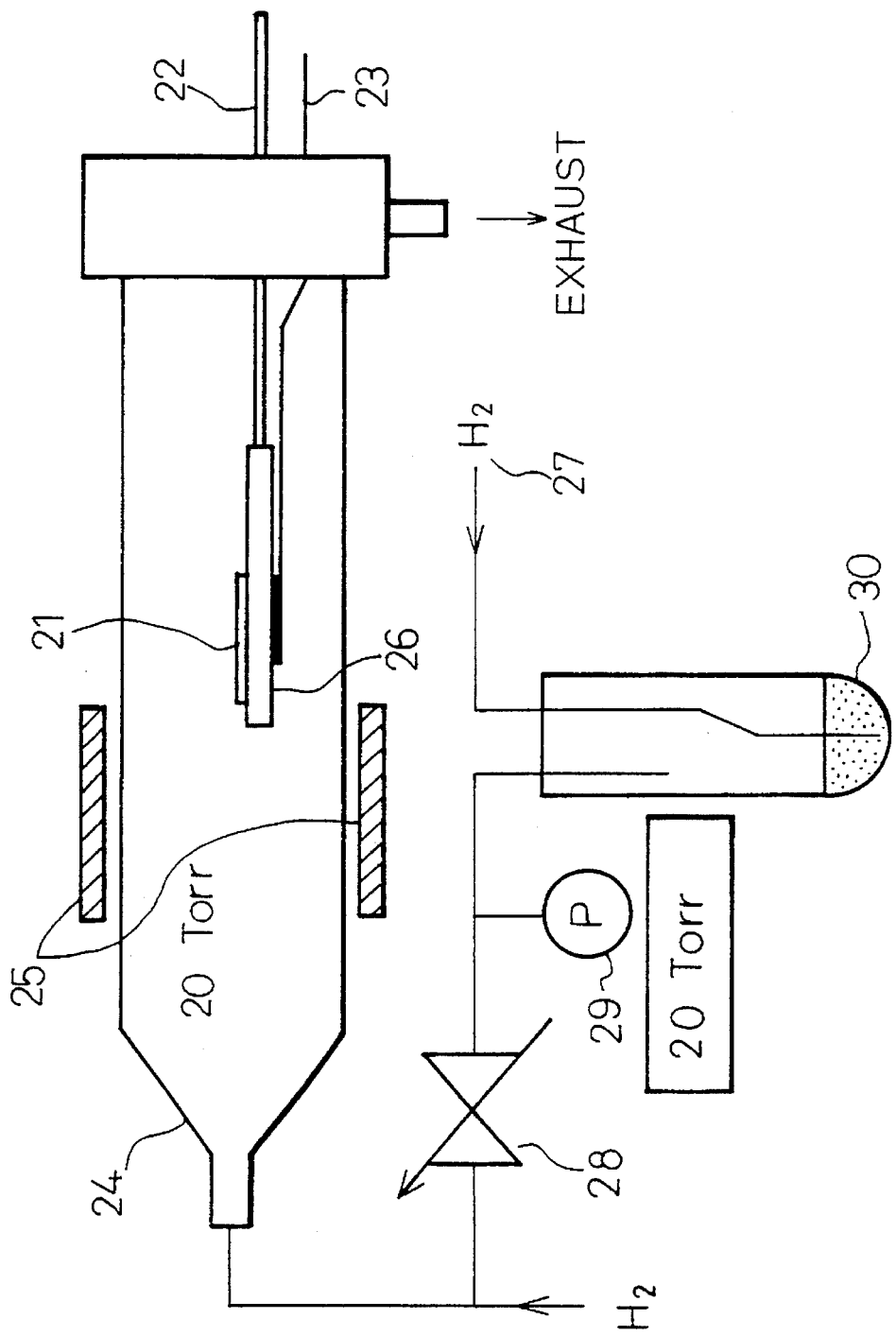
Figure 9:
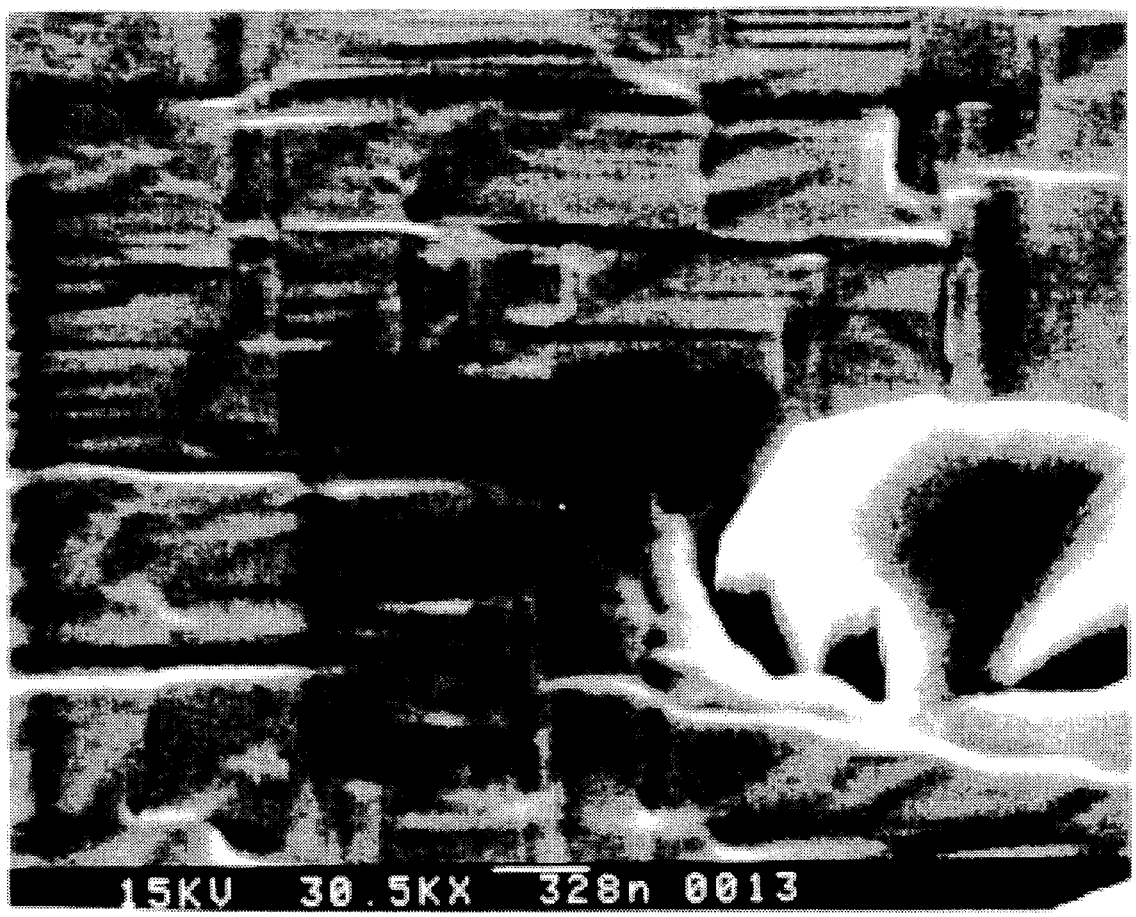
Figure 10:
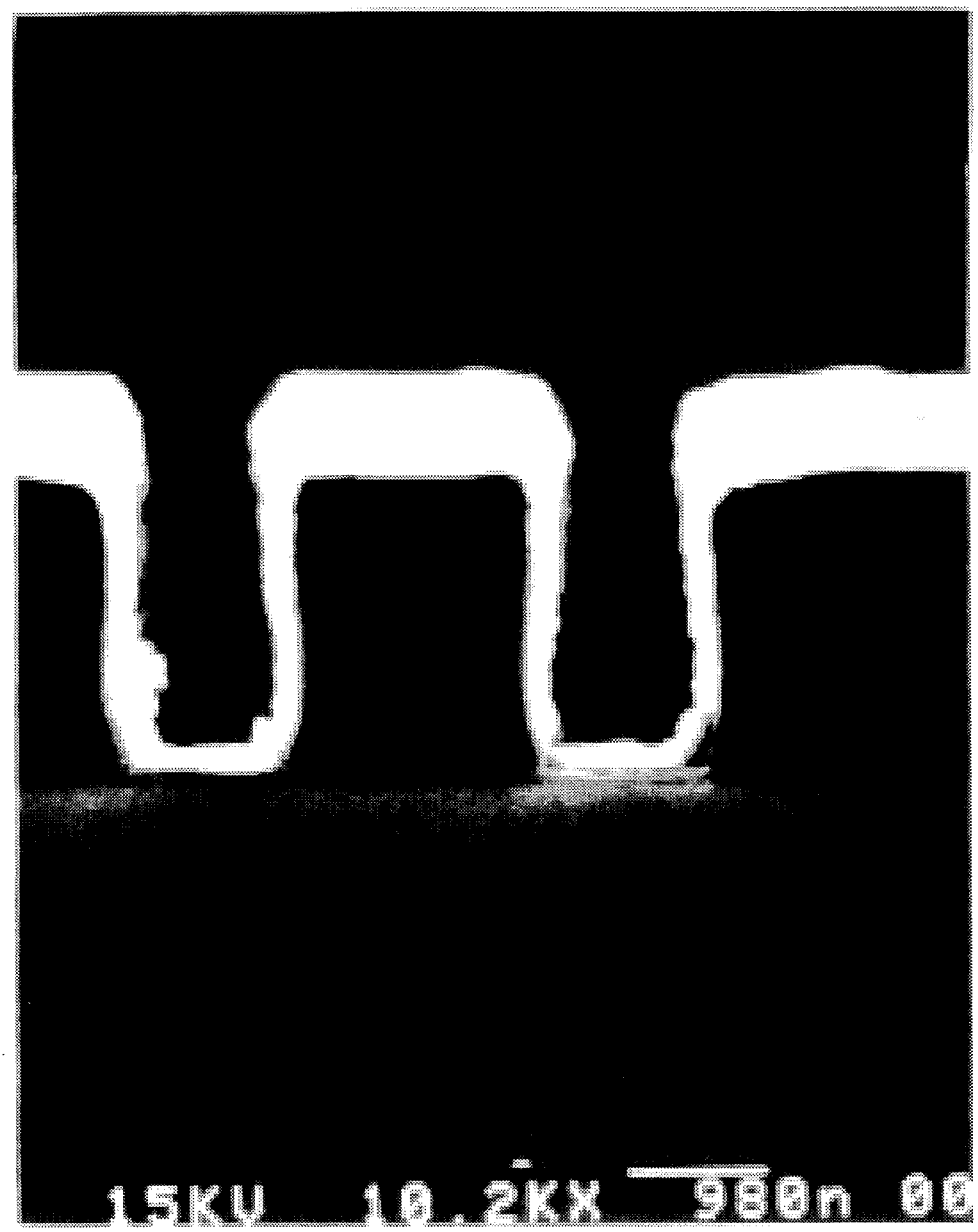
Figure 11:
Figure 12:
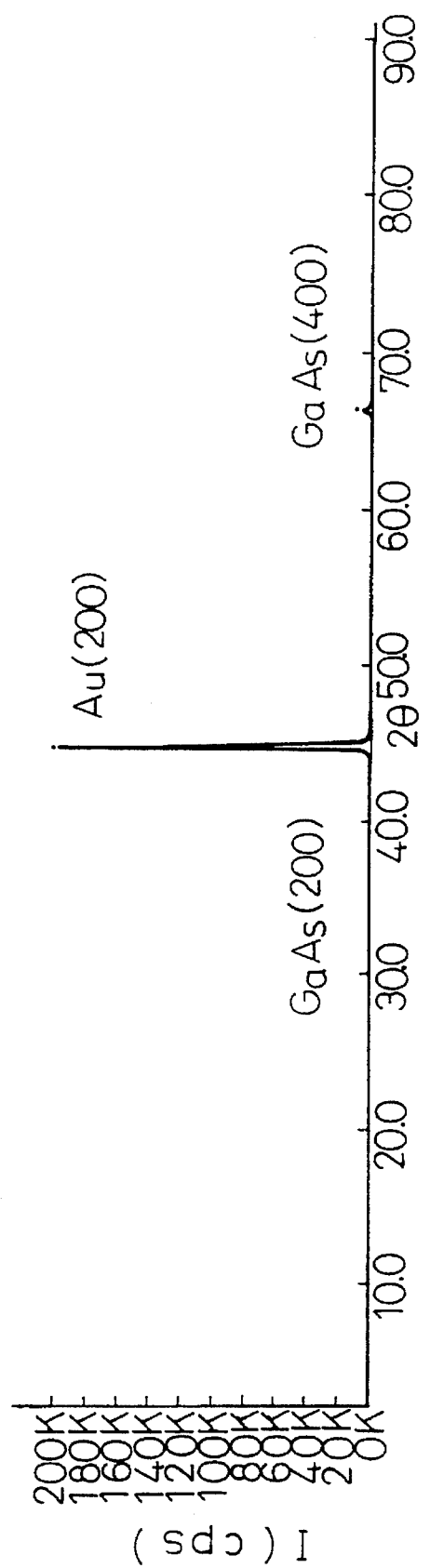
Figure 13:
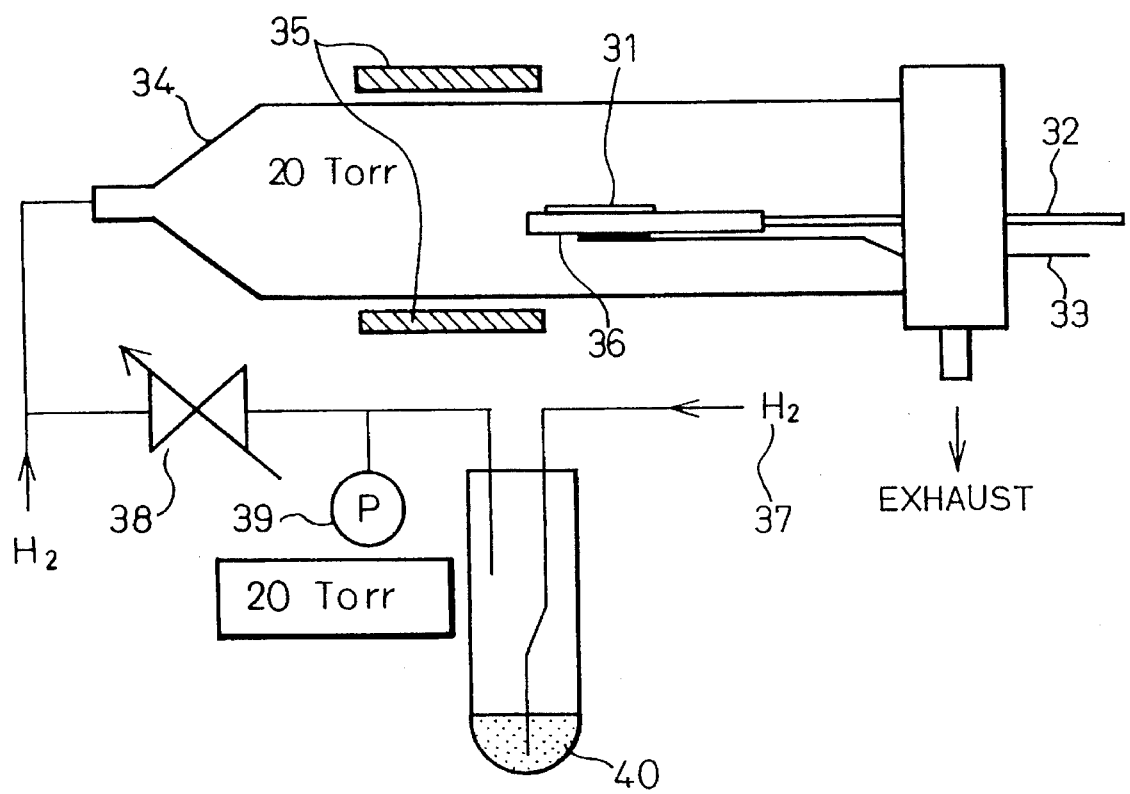
Figure 14:
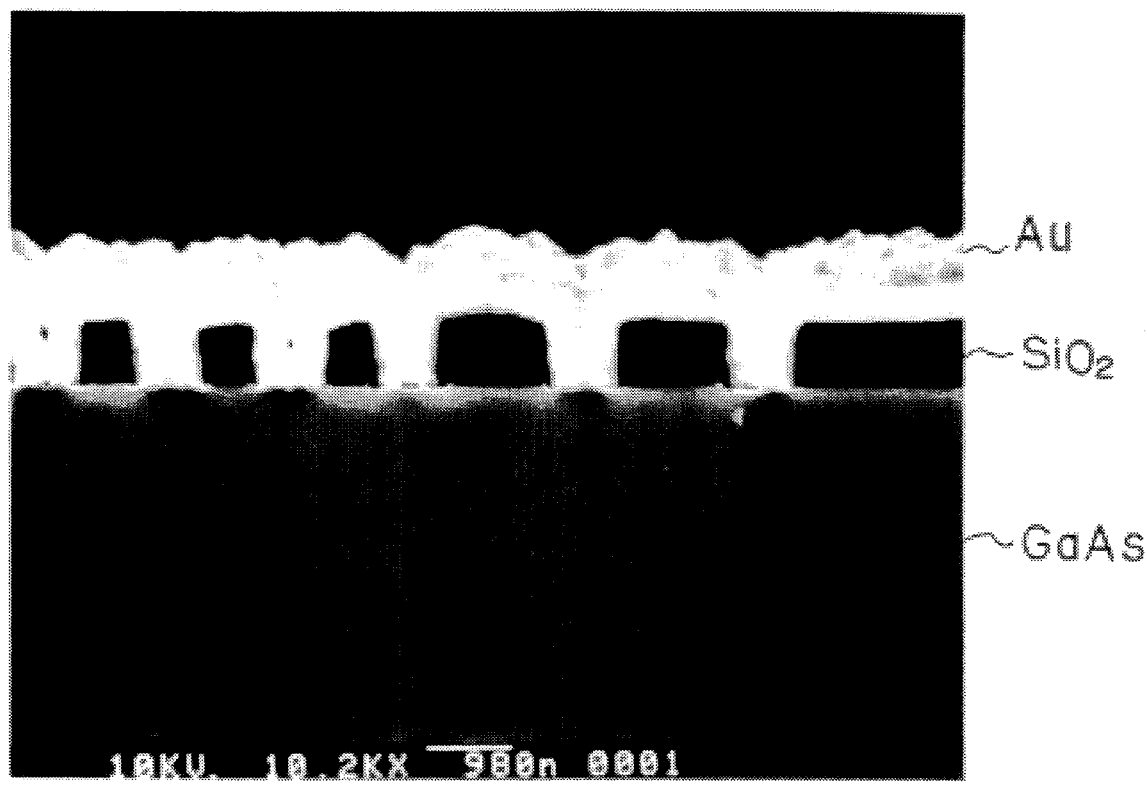
Figure 15:
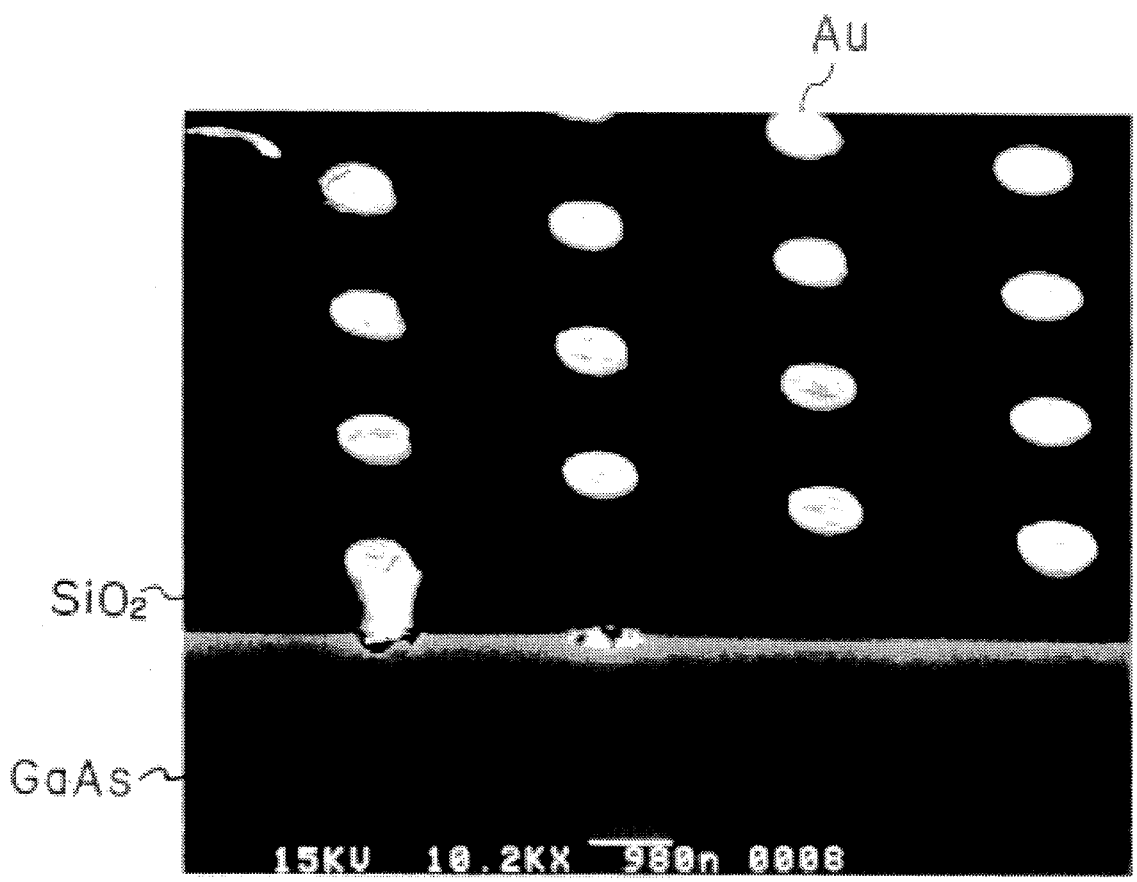
Figure 16:
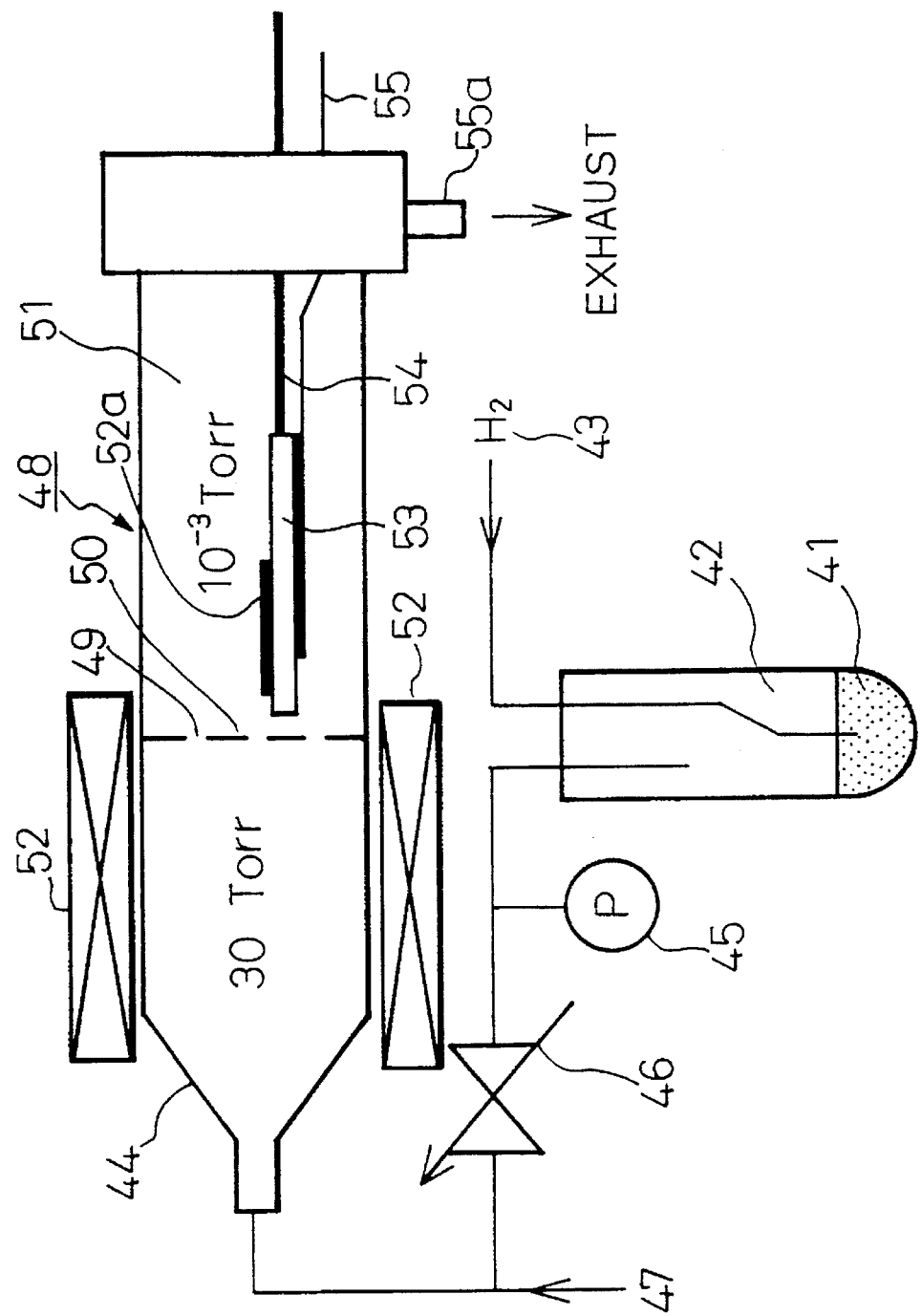
Figure 17:
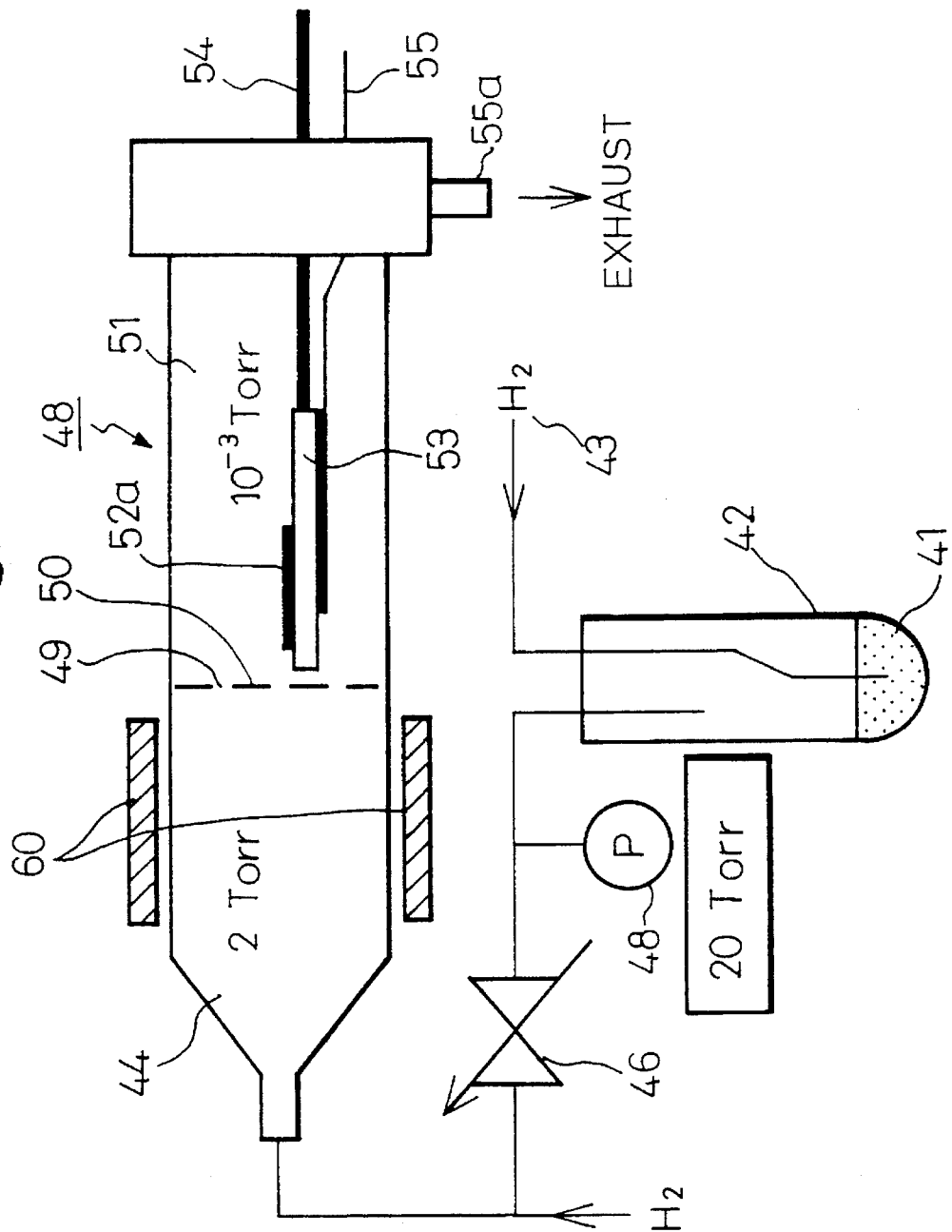
Figure 18:
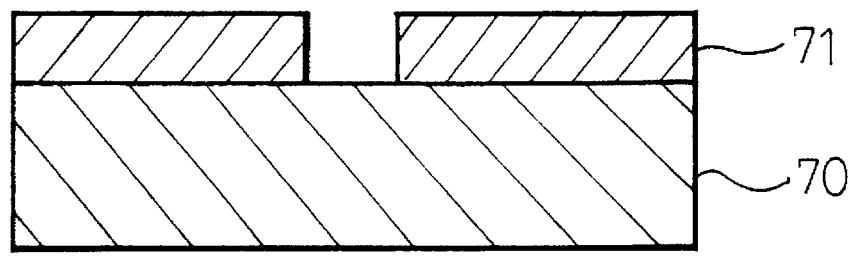
Figure 18:
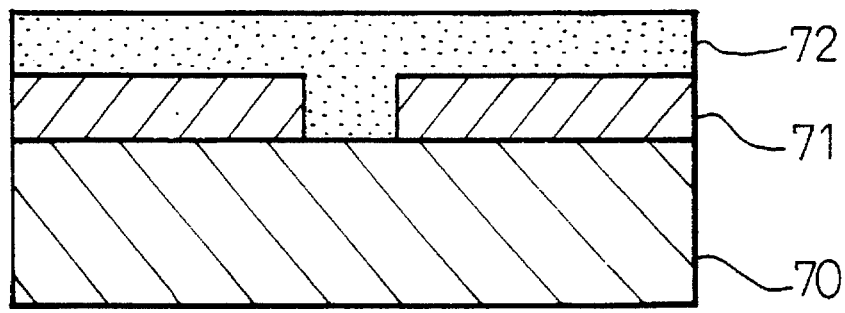
Figure 18:
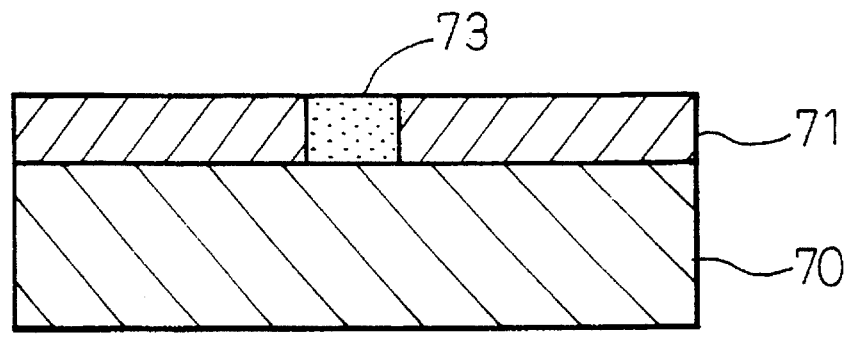
Figure 19:
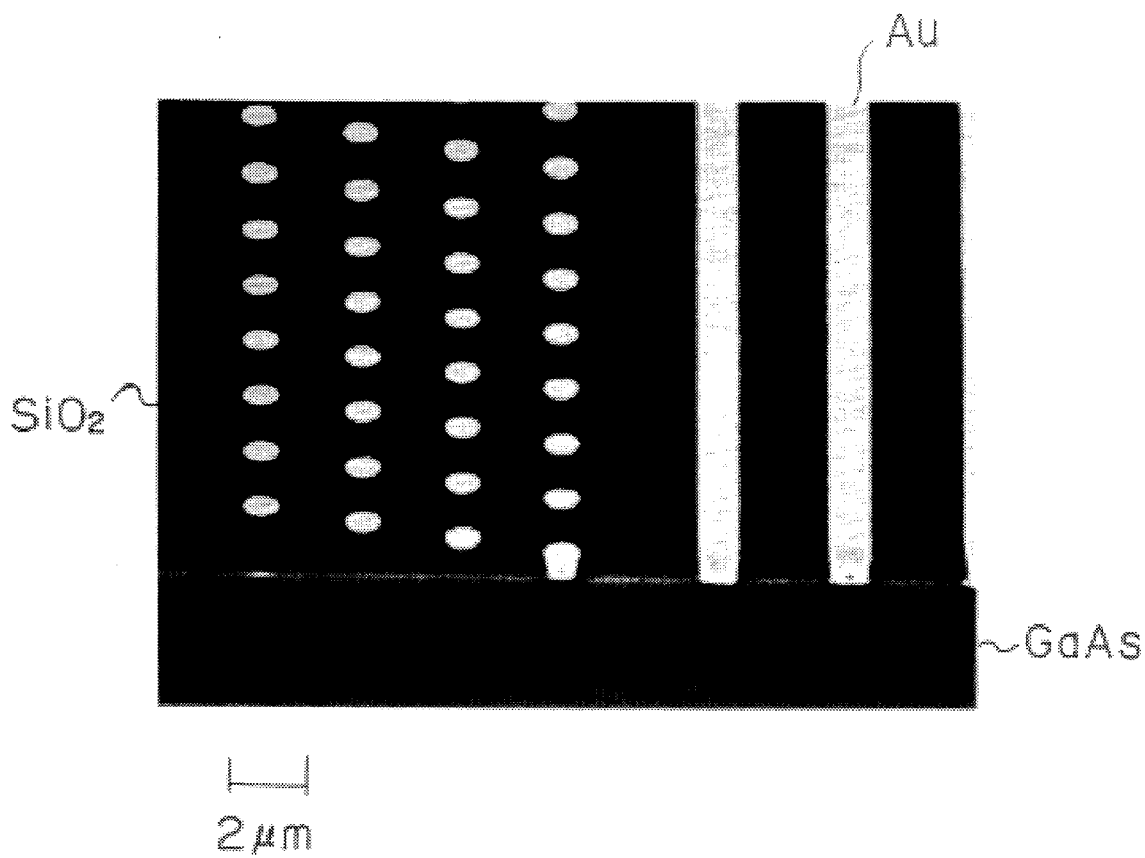

FIGS. 4A($a$), 4A($b$) and 4B($a$) are explanatory views of a model showing the relation between a reaction temperature and a reaction pressure and a growing state of a gold thin film;

FIGS. 5(A), 5(B) and 6 are micrographs of the surface of a gold thin film grown using DMAu (hfac);

FIG. 7 is a micrograph when lines are buried by a gold thin film using DMAu (hfac);

FIG. 8 is an explanatory view explaining the structure of a plasma enhanced CVD apparatus for practicing a method of growing a gold thin film according to the present invention;

FIG. 9 is a micrograph of the surface of a signal-crystal gold thin film;

FIG. 10 is a micrograph showing the cross-section when gold is deposited into lines by plasma CVD;

FIG. 11 is a photograph showing a diffraction pattern of RHEED of single-crystal gold;

FIG. 12 is a diagram showing an X-ray diffraction locking pattern of single-crystal gold;

FIG. 13 is an explanatory view explaining the structure of a plasma/thermal CVD apparatus for practicing a method of growing a gold thin film according to the present invention;

FIG. 14 is a micrograph showing the cross section when gold is buried into $SiO_2$ lines;

FIG. 15 is a micrograph when gold above $SiO_2$ (shown in FIG. 14) is cut off;

FIG. 16 is an explanatory view explaining the structure of a CVD growing apparatus for practicing a method of growing a gold thin film according to the present invention;

FIG. 17 is an explanatory view explaining the structure of a plasma enhanced CVD apparatus for practicing a method of growing a gold thin film according to the present invention;

FIGS. 18(A), 18(B) and 18(C) are cross sectional views showing the stepwise fabrication of a buried type Au wiring; and FIG. 19 is a micrograph showing the state where Au on an insulating film is removed by chemical-mechanical polishing.

DESCRIPTION OF THE PREFERRED EMBODIMENTS

In a method of growing a gold thin film according to the present invention, first means for solving the aforementioned problems uses a starting gas for a gold thin film, and controls an environmental pressure under a reaction rate determining condition so as to form a gold thin film having a flat surface.

According to this first method, dimethylgold hexafluoroacetylacetonato, for example, is used as the starting gas, and a gold thin film having a flat surface is preferably formed in a kinetically controlled region and above 10 Torr of reactor pressure.

Generally, it is common to grow a metal thin film under a low pressure environment, such as the growth of an aluminum thin film, below about 2 Torrs, and the growth of the gold thin film has also been attempted at a low pressure approximate to this pressure.

A series of experiments for growing the gold thin film has been conducted, and it has been discovered that the reactor pressure significantly influences the surface morphology of the grown gold metal.

In the present invention, dimethylgold hexafluoroacetylacetonato (DMAu(hfac)) is used as the starting gas, and the gold thin film is formed by a CVD process under a kinetically controlled region.

Figure 1:
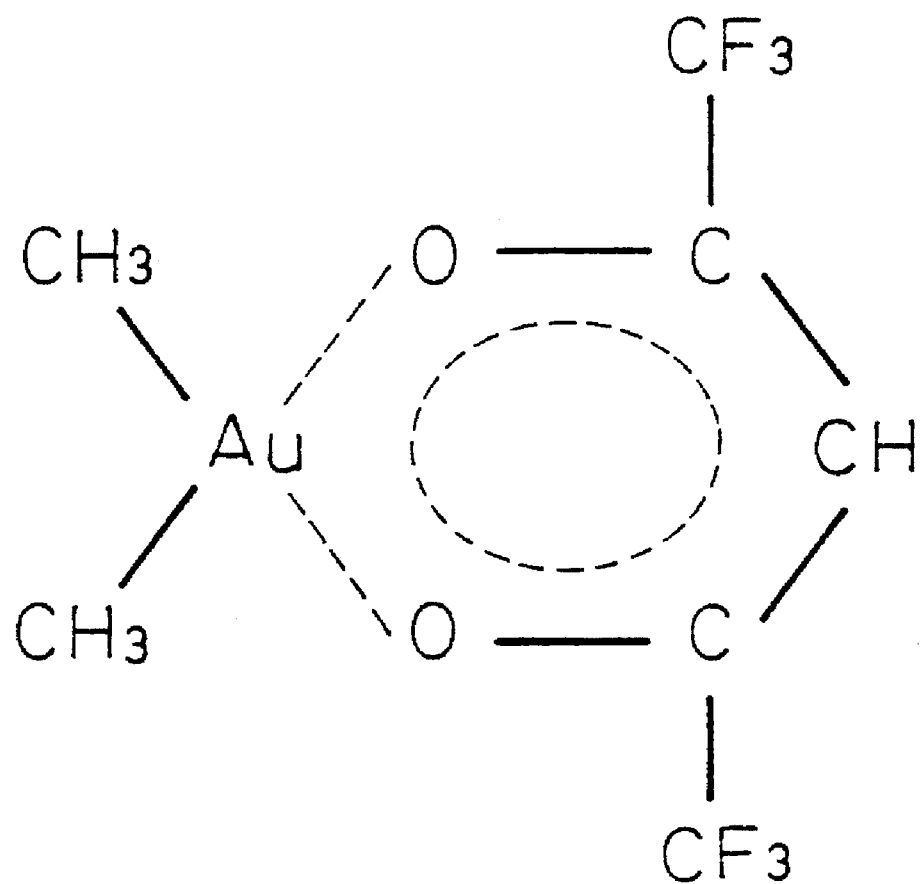
FIG. 1 is a structural diagram of molecules of a starting gas used in the present invention.

FIG. 1 is a structural view showing the molecules of the starting gas used in the present invention.

This starting gas is dimethylgold hexafluoroacetylacetonato (DMAu(hfac)) and its vapor pressure at 24° C. is 400 mTorrs.

Figure 2:
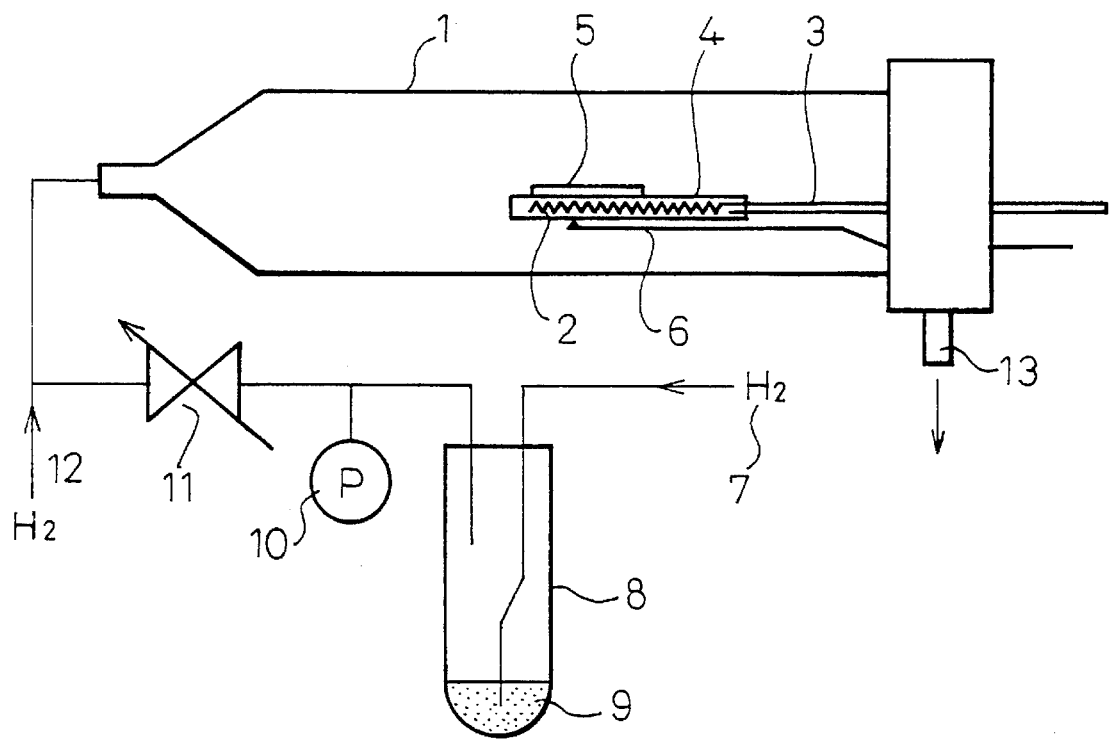
FIG. 2 is an explanatory view explaining the structure of a CVD growing apparatus for practicing a method of growing a gold thin film.

FIG. 2 is an explanatory view explaining the structure of a CVD growing apparatus for practicing the method of growing the gold thin film according to the present invention.

In this drawing, reference numeral 1 denotes a reaction tube, 2 is a heater, 3 is a heater electrode, 4 is a susceptor, 5 is a wafer, 6 is a thermo-couple, 7 is a $H_2$ carrier gas, 8 is a bubbler, 9 is DMAu (hfac), 10 is a pressure gauge, 11 is a variable conductance valve, 12 is diluting $H_2$, and 13 is an exhaust port.

In the CVD growing apparatus for practicing the formation method of the gold thin film of the present invention, the wafer 5 is supported inside the reaction tube 1 by the susceptor 4 having the heater 2 and the heater electrode 3 as shown in the drawing, and the temperature of the susceptor 4 is measured by the thermo-couple 6. On the other hand, the $H_2$ carrier gas 7 is passed through DMAu(hfac) 9 inside the bubbler 8, and while the pressure of the $H_2$ carrier gas 7 containing DMAu(hfac) therein is being monitored by the pressure gauge 10, the gas is introduced into the reaction tube 1 by regulating the flow rate by the variable conductance valve 11. If necessary, diluted $H_2$ 12 is also introduced into the reaction tube 1, and an exhaust gas is discharged from the exhaust port 13.

Figure 3:
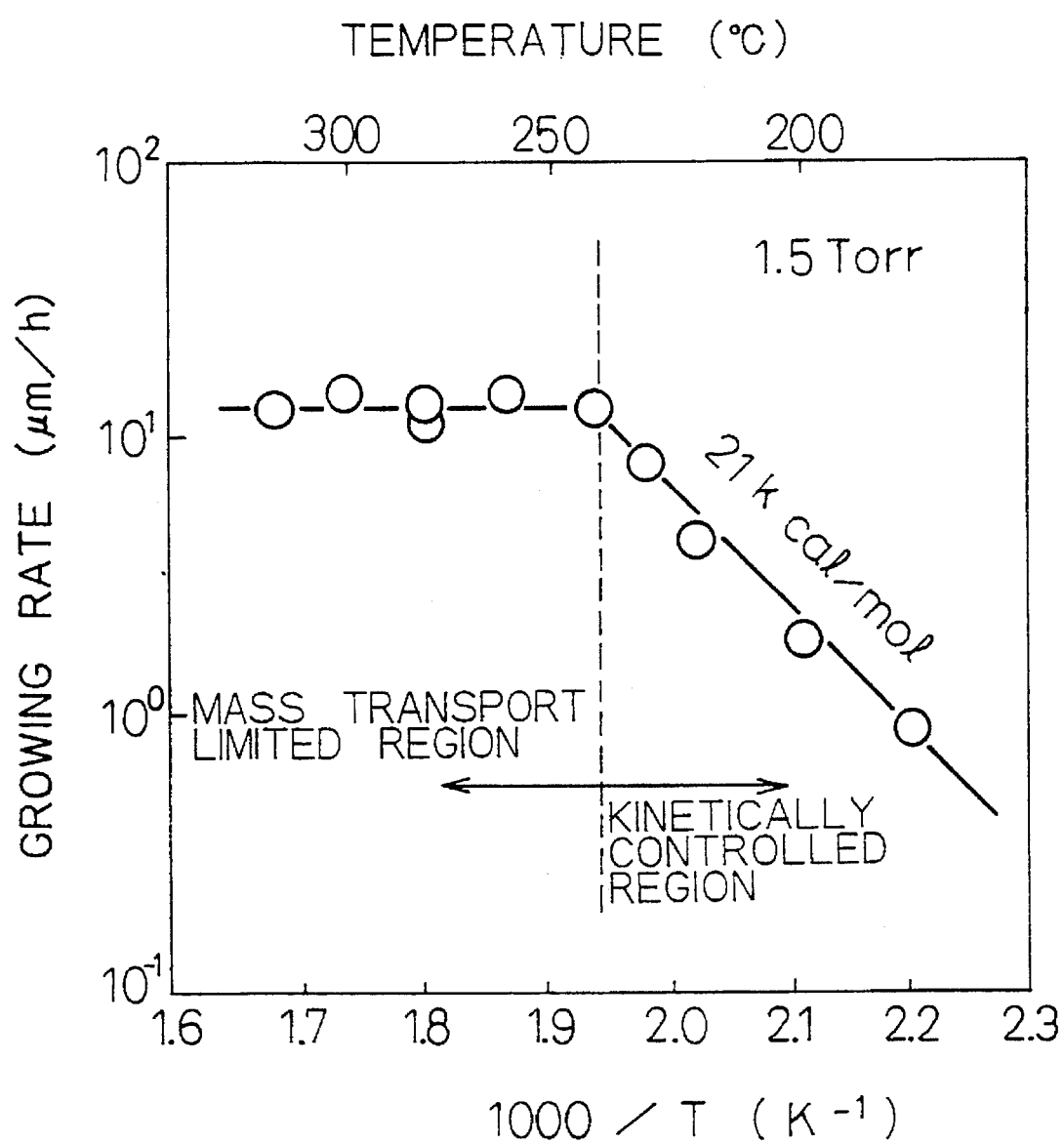
FIG. 3 is a diagram showing the relation between a growing temperature and a growth rate of a gold thin film.

FIG. 3 is a diagram showing the relation between the growing temperature and the growth rate of the gold thin film.

The horizontal axis represents the reciprocal temperature (1,000/T ($K^{-1}$),° C.), and the ordinate represents the growth rate (μm/hr).

In FIG. 3, the relation between the growth temperature and the growth rate of the gold thin film is obviously divided into a kinetically controlled region below 240° C. and a mass transport limited region above 240° C.

In the mass transport limited region higher than 240° C., the growth remains substantially constant irrespective of the growth temperature, and in the kinetically controlled region lower than 240° C., the growth rate decreases with the decrease of the reaction temperature.

In the mass transport limited region, the mass transport rate of the starting molecules determines the reaction where the reaction rate is high. Accordingly, undecomposed DMAu(hfac) hardly exists in the vapor phase and does not reach the substrate surface.

In the kinetically controlled region, on the other hand, the reaction rate determines the growth rate, and the transportation of the starting molecules becomes excessive. Accordingly, undecomposed DMAu(hfac) exists in the gas phase and reaches the substrate.

FIG. 4(A) through 4(C) are explanatory view of model explaining the relation between the growth temperature and the reactor pressure versus the growing state of the gold thin film.

The growing state of the gold thin film under each reaction condition shown in the diagram will be explained.

I. Reaction rate determining range:
   A low pressure (1.5 Torrs):
   DMAu(hfac) under a low temperature state reaches the substrate undecomposed, and is decomposed at a specific site of the substrate.
   Since DMAu(hfac) has a long migration distance after adhering to the surface of the substrate, a needle-like crystal having a (100) plane having a low growth rate is grown.
   Migration occurs over a long distance, a needle-like crystal is formed and the formation density of a nucleus is small. Therefore, a continuous gold thin film cannot be obtained.
   Accordingly, the gold thin film grown under these conditions is not suitable for a wiring layer of an LSI, and the like.

B. high pressure (30 Torrs or above):
   DMAu(hfac) molecule at a low temperature and a medium pressure impinges frequently against the hydrogen molecules in the gas phase. Accordingly, it reaches the substrate in a medium decomposed state, adheres to the surface of the substrate without selecting the site, and migrates only over a medium distance.
   Accordingly, the needle-like crystal does not grow on the surface of the gold thin film, the formation density of the nucleus is large, and a continuous gold thin film having a substantially uniform thickness can be obtained.
   The gold thin film grown under these conditions is suitable for the wiring layer of the LSI, and the like.

II. Transport rate determining range:
   C. low pressure (1.5 Torrs):
   Upon being exposed to a high temperature, DMAu(hfac) reaches the substrate in a heavily decomposed state. Accordingly, its migration distance after adhering to the surface of the substrate is small, and it cannot migrate to the step of the surface of the substrate, and once adhering to a terrace, it continues to grow on the (111) plane.
   Therefore, a round crystal having a dull crystalline surface grows, and the gold thin film is not suitable for the wiring layer of the LSI, and the like.

The result of the examination of FIGS. 3 through 4(C) and the observation obtained from a large number of experiments carried out in connection with FIGS. 3 through 4(C) provide the following conclusion on the growth of the gold thin film using DMAu(hfac).

1. To obtain a continuous gold thin film having a large formation density of nucleus and a substantially uniform thickness without generating a needle-like crystal on the surface, undecomposed DMAu(hfac), which does not select a site and which migrates over a medium distance after adhering to the surface of the substrate, must exist in the gas phase just above the substrate surface.

2. This condition occurs in the kinetically controlled region where the transport rate of the starting molecules is excessive with respect to the reaction rate.

The second means for solving the aforementioned problems according to the present invention is to use low energy plasma to such an extent as not to completely decompose the starting gas for forming the gold thin film, and the resulting partially decomposed starting gas is fed to the substrate to form a single crystal gold thin film having a flat surface on the single crystal substrate.

In this second means, too, dimethylgold hexafluoroacetylacetonato, for example, can preferably be used as the starting gas.

Since the lower energy plasma not completely decomposing the starting gas molecules is added in this second means, a uniform single crystal gold thin film can be formed.

Motion of the starting molecules is made more vigorous on the substrate by imparting low plasma energy as described above, and a single crystal grows epitaxially on the substrate. Since the low energy plasma is used, the starting molecules are not completely decomposed and the partially decomposed gas can reach the bottom of lines. In this way, a single crystal film having excellent step coverage can be obtained. Since the single crystal film can be formed, resistance to electromigration can further be improved.

Next, the present invention proposes the third means for further improving the effect of the first means.

In other words, when the thermal CVD process (the first means) for completely burying the lines or bias is employed, a film having adhesion to a certain extent can be obtained, but this adhesion is not yet sufficient.

To prepare a film having high adhesion, it has been necessary conventionally to etch in-situ the substrate in Al-CVD or to grow in-situ other metals. For this reason, an etching gas having high reactivity, which is difficult to handle, and a growing gas for other metals, become necessary. Though a film having high adhesion can be obtained by plasma enhanced CVD, its step coverage is inferior to that of thermal CVD.

There has been a strong demand for a method that can bury the lines or bias without effecting in-situ etching of the substrate and in-situ growing of other metals, and that can moreover form a film having high adhesion with the substrate. The demand for an improvement in step coverage is also strong. The third means of the invention satisfies these requirements.

In the gold thin metal vapor growing method of the first means, this third means is characterized in that a first gold thin film having high adhesion with the substrate is formed by plasma enhanced CVD, and a second gold thin film is subsequently formed by thermal CVD on the first gold thin film.

As described above, the third means forms the first gold thin film having high adhesion on the substrate by plasma enhanced CVD prior to thermal CVD.

In other words, motion of the metal molecules on the substrate is activated by imparting plasma energy, so that the reaction with the substrate at deep portions from the surface, and adhesion with the substrate can be improved. Since the surface of this gold thin film is clean, the thermal excitation CVD film strongly grows with a high degree of adhesion. When the film thickness of the film grown by plasma CVD is made smaller than the thickness of the film grown by thermal excitation CVD, it is possible to prevent the open portions of the lines from being closed with the metal while the lower portions of the lines are left unburied.

Preferably, the gas for forming the gold thin film is dimethylgold hexafluoroacetylacetonato.

Next, the present invention proposes a fourth means for further improving the effect of the first or second means thereof.

The object of using this fourth means is to provide a gold thin film vapor growing method that can make the decomposition state of the starting gas uniform upon its arrival at the substrate and that can obtain a gold thin film having a flat surface.

According to this fourth means, the starting gas is decomposed by either the thermal CVD process of the first means or by the plasma enhanced CVD process of the second means so as to form an intermediate product, and the resulting intermediate product is transferred to the gold thin film growing portion to form the gold thin film on the substrate.

In other words, the gold thin film vapor growing method as the fourth means when utilizing the thermal CVD process pre-heats the starting gas for forming the gold thin film at a pressure within the range of about 10 to about 100 Torrs and at a temperature within the range of about 150° to about 240° C. to decompose the starting gas and to form an intermediate product, and jets out the resulting intermediate product to a substrate, on which the film is to be formed, in a vacuum of up to about $10^{-3}$ Torrs to form the gold thin film on the substrate.

The fourth means of utilizing the plasma enhanced CVD is that the starting gas is under a pressure state of up to 10 Torrs, and plasma is generated at room temperature so as to form an intermediate product, and the resulting intermediate product is jetted out to the substrate placed in a vacuum of up to about $10^{-3}$ Torrs to form the gold thin film on the substrate.

In the fourth means, the starting gas is preferably dimethylgold hexafluoroacetyclacetonato.

As described above, the present invention using the fourth means decomposes in advance the starting gas by the predetermined thermal CVD process or by the predetermined plasma enhanced CVD process to form the intermediate product. Consequently, the present invention can bring inflowing starting gas into the optimum decomposition state. Since the resulting intermediate product is jetted to the substrate in a vacuum state, the intermediate product can reach the substrate without changing its decomposition state, and the gold thin film having a flat surface can be formed on the substrate.

Finally, an invention that forms a buried type gold (Au) very thin wire and column by burying the growth of gold utilizing the present invention will be explained.

The gold very thin wire can be used as an LSI wiring and an X-ray lithography mask. The gold column can be used as a contact material of a through-hole of the LSI. In the LSI wiring, Au has a lower resistance than Al and W, a higher melting point and a greater atomic weight. Therefore, gold is believed to be superior in electromigration resistance relative to Al. Since gold has high malleability, it is also expected to be highly resistant to stress migration. Gold has higher corrosion resistance than other metals and has a high degree of reliability for a long time. It is therefore a necessary material for an LSI chip which is to be mounted to an apparatus used under in a corrosive environment such as a submarine cable. The Au very thin wire has high utility as a mask for X-ray lithography. Conventionally, the Au very thin wire has been formed by Ar ion milling of Au grown by sputtering, or by selective growth of a plating. When the very thin wire (~0.25 μm) is etched by Ar ion milling, a flat cut surface can not be made and also the sectional shape of a metal film pattern undergoes deformation to a trapezoidal shape. Accordingly, it has been very difficult to obtain a pattern with an aspect ratio (a ratio of a longitudinal length to a transverse length) with a thickness sufficient enough to absorb the X-rays and capable of satisfying very fine pattern dimensions.

An admixture of impurities into the film is vigorous in sputtering and plating, particularly in plating. Therefore, an increase in electric resistance and the generation of radiation occur, thereby reducing performance of the LSI.

To solve these problems, the Au very thin wire or column which is buried in other material is formed in lines or bias in a thin film or semiconductor flatly deposited on the substrate, growing Au over the entire surface by the CVD process, and removing Au by polishing which exists on the upper part of thin films or the semiconductor.

When Au is polished in this case, a polishing solution is prepared by mixing an aqueous KI and $I_2$ solution kept at a predetermined temperature with very fine abrasive powder not reacting with this solution.

Hereinafter, the present invention will be explained in further detail with reference to Examples thereof. Needless to say, however, the present invention is in no way limited to these Examples.

EXAMPLE 1

The experiment that grew a gold thin film using DMAu-(hfac) as the starting material, as the first means and as the basis of the present invention, will be explained with reference to micrographs.

FIGS. 5(A), 5(B) and 6 are micrographs of the surfaces of the gold thin films grown using DMAu(hfac).

Each growing condition and the surface condition of the gold thin film grown under such a condition will be explained with reference to these micrographs.

This experiment was carried out using the CVD growing apparatus previously shown in FIG. 2 and a cold wall type reaction tube for directly heating the substrate by a heater by changing the growing conditions within the following ranges.

| | |
|---|---|
| growth pressure: | 1.5 to 100 Torr |
| growth temperature: | 180 to 320° C. |
| bubbler temperature: | 20° C. |
| bubbling pressure: | 20 to 103 Torr |
| bubbling flow rate ($H_2$): | 200 sccm |
| diluting $H_2$: | 50 sccm |
| substrate: | $SiO_2$/Ti/GaAs |
| First set of conditions (refer to FIG. 5(A)): | |
| substrate temperature: | 240° C. |
| reactor pressure: | 1.5 Torr |
| surface morphology of gold thin film: A large number of needle-like crystals grew. | |
| Second set of conditions (refer to FIG. 5(B)): | |
| substrate temperature: | 240° C. |
| reactor pressure: | 10 Torr |
| surface morphology of gold thin film: The density of needle-like crystals was reduced to 1/3 of the number of film ground of the first set of conditions. | |
| Third set of conditions (refer to FIG. 6): | |
| substrate temperature: | 240° C. |
| reactor pressure: | 30 to 50 Torr |
| surface morphology of gold thin film: A flat surface could be obtained without the generation of needle-like crystals. | |

It can be understood from the micrographs of the experiments described above that a gold thin film having a flat surface could be obtained under the third set of conditions, where the substrate temperature was 240° C. and the reactor pressure was from 30 to 50 Torr, without generating the needle-like crystals (refer to FIG. 6). As a result of the experiments, a substantially flat gold thin film could be obtained at an reactor pressure within the range of 10 to 100 Torr.

The flat surface gold thin film such as those shown in the micrographs could also be obtained at the substrate temperature of not higher than 240° C.

FIG. 7 is a micrograph when lines were buried by the gold thin film using DMAu(hfac).

The growing conditions in this case were a substrate temperature of 230° C. and an reactor pressure of 30 Torr. The substrate was made of GaAs, the lower layer wiring layer was made of Ti, and the insulating film having contact holes was made of $SiO_2$.

As can be seen from the micrograph, gold was completely buried in the lines, grew flat on the $SiO_2$ insulating film and was confirmed to be excellent as the wiring layer.

EXAMPLE 2

Next, an example of the gold thin film vapor growing method as the second means will be explained.

FIG. 8 is an explanatory view explaining the structure of a plasma CVD apparatus for executing the gold thin film growing method according to the present invention.

In the drawing, reference numeral 21 denotes the substrate, 22 is an electrode, 23 is a thermo-couple, 24 is a reaction tube, 25 is a radio frequency (RF) electrode, 26 is a heater, 27 is a carrier gas ($H_2$), 28 is a variable conductance valve, 29 is a pressure gauge, and 30 is DMAu(hfac) as the starting material. Unlike the thermal CVD growing apparatus previously described, this plasma enhanced CVD apparatus is equipped with the RF electrode 25. With the RF electrode 25, plasma is generated and affects the reaction and a uniform thin film is formed on the substrate. The remaining elements are substantially the same as the foregoing thermal CVD growing apparatus and hence, the explanation will be omitted.

The growing method of the gold thin film using this apparatus will be explained with reference to an example. The starting material 30 was dimethylgold hexafluoroacetylacetonato (DMAu(hfac)). This starting DMAu(hfac) was transported to the reaction tube 24 using hydrogen ($H_2$) as the carrier gas. A bubbler pressure was 20 Torrs, and the temperature was 20° C. The $H_2$ gas flow rate was 20 sccm. Growth was carried out by the plasma of 13.56 MHz and 8 W output. The DMAu(hfac) molecules were not completely decomposed by this plasma energy. The growth temperature was 200° C., and this temperature prevented the DMAu(hfac) molecules from decomposing completely. In the case of thermal CVD, a temperature below 240° C. was a kinetically controlled region. The substrate 21 was an LEC grown GaAs (100) semi-insulating substrate. The growing rate was 2.2 μm/hr.

FIG. 9 is an SEM (Scanning Electron Microscopy) micrograph of the surface of the gold thin film thus grown. The surface having a regular tile-like arrangement suggested that the crystal was a single crystal.

FIG. 10 is an SEM micrograph of the section of the gold thin film deposited into the line. As can be clearly seen from this micrograph, the gold thin film having excellent step coverage was grown.

FIG. 11 is a photograph showing a diffraction pattern of reflection high energy electron diffraction (RHEED). The spotty pattern in the photograph evidences that the resulting crystal was a single crystal.

FIG. 12 shows an X-ray diffraction locking pattern. It can be appreciated from this pattern that the gold thin film had the same (100) orientation as GaAs. It could be confirmed from the diffraction pattern of RHEED shown in FIG. 11 and from the X-ray diffraction locking pattern shown in FIG. 12 that the gold thin film had the same direction as GaAs of the substrate having Au(100)//GaAs(100), Au(110)//GaAs(110).

As can be clearly appreciated from this Example, the method of the present invention can form a single crystal having excellent step coverage on the single crystal substrate. Such a single crystal has a far higher migration resistance than polycrystal and is extremely effective as a wiring material.

EXAMPLE 3

Hereinafter, the gold thin film vapor growing method as the third means of the invention will be explained.

FIG. 13 is an explanatory view explaining the structure of a plasma enhanced CVD/thermal CVD apparatus for executing the gold thin film growing method according to the present invention.

In the drawing, reference numeral 31 denotes a substrate, 32 is an electrode, 33 is a thermo-couple, 34 is a reaction tube, 35 is a radio frequency (RF) electrode, 36 is a heater, 37 is a carrier gas ($H_2$), 38 is a variable conductance valve, 39 is a pressure gauge, and 40 is DMAu(hfac) as the starting material.

An example of the growth of the gold thin film using this apparatus will be explained.

The starting gas was DMAu(hfac), which was transported to the reaction tube 34 using hydrogen as the carrier gas. The bubbler pressure was 20 Torrs, and the temperature was 20° C. The $H_2$ gas flow rate was 20 sccm. The growth pressure was 2 Torrs, and the growth temperature was 200° C. Growth of the gold thin film was carried out using a plasma of 13.56 Mhz and 8W output. The substrate 31 was LEC grown GaAs (100) semi-insulating substrate. The growth time was 5 minutes. In this way, the plasma enhanced CVD process was completed. Immediately thereafter, thermal CVD was carried out in-situ. The $H_2$ gas flow rate to the bubbler was 200 sccm. The growth pressure was 30 Torrs and the growth temperature was 240° C. The substrate 31 was likewise an LEC grown GaAs(100) semi-insulating substrate. The growth time was 10 minutes.

FIG. 14 is a micrograph of the cross section when gold was buried into lines disposed in $SiO_2$ using the method described above. FIG. 15 is a micrograph when gold (Au) at the upper part of $SiO_2$ in FIG. 14 was scraped off, thereby evidencing high adhesion with the GaAs substrate. It can be appreciated from FIG. 14 that gold remained only in the bias portions because the gold thin film had high adhesion with the GaAs substrate, though it has low adhesion with $SiO_2$. High adhesion was also confirmed for gold coating on GaAs of the substrate.

EXAMPLE 4

Next, an example of the gold thin metal vapor growing method as the fourth means of the present invention will be explained, but use of the thermal CVD process will first be explained.

In a gold thin film vapor growing apparatus shown in FIG. 16, dimethylgold hexafluoroacetylacetonato (DMAu(hfac)) was stored in the bubbler 42, and a feed passage of the $H_2$ carrier gas 43 was communicated with this bubbler 42.

The pressure gauge 45 for measuring the internal pressure of the bubbler 42 and the variable conductance valve 46 for regulating the feed quantity of the starting gas are disposed in the starting gas feed passage extending from the bubbler 42 to the intermediate production formation portion 44, and a feed passage of the diluting $H_2$ gas 47 to be added to the starting gas is further disposed, whenever necessary.

The reaction tube 48 is divided by the intermediate production formation portion 44 and the gold thin film growing portion 51 by a separation plate having jet ports 49 formed therein.

A heater 52 for pre-heating is disposed round the outer periphery of the intermediate product formation portion 44, and is kept at a relatively high pressure, as will be described subsequently, so that the starting gas can be decomposed into the intermediate product by preliminary heating.

A substrate 52a on which the gold thin film is to be formed is disposed inside the gold thin film formation portion 51. A heater 53 and a heater electrode 54 are also disposed in this portion 51 in such a manner as to support the substrate 52a. An exposed port 55a is defined on the opposite side of the separation plate 50 in the gold thin film formation portion 51.

Next, the gold thin film vapor growing method of this Example will be explained.

Dimethylgold hexafluoroacetylacetonato (DMAu(hfac)) as the starting material 41 was stored in the bubbler 42. The $H_2$ carrier gas 43 was introduced into this bubbler 42 and the starting gas was sent into the intermediate product formation portion 44 of the reaction tube 48. In this instance, the pressure inside the bubbler 42 was monitored by the pressure gauge 45 and was regulated so that the pressure inside the intermediate production formation portion 44 was within the range of from about 10 to about 100 Torrs, such as 30 Torrs. The temperature inside the intermediate product formation portion 44 was controlled by the heater 52 to a temperature within the range of about 150° to about 240° C.

After the pressure and the temperature were thus regulated, the starting gas inside the intermediate product formation portion 44 was partially decomposed to provide an intermediate product. Since the pressure and the temperature inside the intermediate product formation portion 44 were constant, a decomposition state to the intermediate product became homogeneous. The intermediate product was believed to be a material under the state where radicals $CH_3$— and $CF_3$— were taken off from the starting material shown in FIG. 1.

On the other hand, the gold thin film growing portion 51 was adjusted to a high vacuum state of up to about $10^{-3}$ Torrs. Accordingly, the intermediate product in the intermediate product formation portion 44 was jetted from the exhaust port 49 of the separation plate 50 disposed between the intermediate product formation portion 44 and the gold thin film formation portion 51 into the gold thin film growing portion 51. Since the gold thin film growing portion 51 was kept under the high vacuum state, the intermediate product thus jetted out reached the substrate 52a without being affected by its molecular state.

The substrate 52a was heated by the heater 53, and its temperature was controlled to the same temperature as the internal temperature of the intermediate product formation portion 44 within the range of about 150° to about 240° C. Therefore, the intermediate product reaching the substrate 52a was thermally decomposed, and a gold thin film having a flat surface was formed on the substrate 52a.

The temperature of the heater 53 was measured by the thermo-couple 55, and unnecessary materials after thermal decomposition were discharged through the exhaust port 55a.

According to this Example, the starting gas for forming the gold thin film was preliminarily heated at a pressure within the range of about 10 to about 100 Torts and a temperature within the range of about 150° to about 240° C.

and was decomposed to provide the intermediate product. Accordingly, the inflowing starting gas could be decomposed to the most appropriate decomposition state. Since the intermediate product thus formed was jetted to the substrate kept under the high vacuum state, the intermediate product could reach the substrate without changing its decomposition state, and the gold thin film having a flat surface could be formed on the substrate.

The Example given above aimed at making the decomposition state of the starting gas homogeneous by forming in advance the intermediate product by pre-heating and forming a gold thin film having a flat surface on the substrate. Next, an Example for advance forming the intermediate product by utilizing the plasma enhanced CVD process will be briefly explained.

The apparatus used in this case was substantially the same as the CVD growing apparatus shown in FIG. 16 except that an electrode 60 for generating a radio frequency was disposed in place of the heater 52 of the CVD growing apparatus. Therefore, reference numerals used in FIG. 17 corresponding to those used in FIG. 16 and their explanation, will be omitted.

The intermediate product generation portion 44 was kept at 2 Torrs, and hydrogen plasma was generated at room temperature by the operation of the RF generation electrode 60. DMAu(hfac), as the starting gas, was sent to the intermediate product formation portion 44 using hydrogen as the carrier gas. The molecules of the starting gas were partially decomposed in this intermediate product formation portion 44, and the intermediate product was formed. The resulting intermediate product was sent into the gold thin film growing portion 51 kept within the growing range ($10^{-3}$ Torrs). Since the gas was a molecular flow in this gold thin film growing portion 51, the intermediate product formed in the low pressure intermediate product formation portion reached the substrate 52a without any change. The starting material was sent directly out to the substrate from the region in which the hydrogen plasma was homogeneously applied thereto. For this reason, the decomposition degree of the intermediate product could be controlled to a certain degree.

As can be understood clearly from the Example given above, the method of this Example can preferably control the decomposition state of the starting molecules. Accordingly, the optimum growth conditions can be employed, and hence, the gold thin film having a flat surface can be grown with a high degree of controllability.

EXAMPLE 5

The formation of an LSI wiring by burying the growth of gold will be explained with reference to FIG. 18.

First of all, an insulating film 71 of $SiO_2$ or SiON was formed on a substrate 70 of Si, etc., by plasma enhanced CVD, and lines and bias were formed in the insulating film 71 by etching using a resist pattern (FIG. 18(A)). Next, the blanket growth of an Au thin film 72 was carried out according to the plasma enhanced CVD/thermal CVD process as the third means previously explained (FIG. 18(B)). The growing condition was the same as that of Example 3. An aqueous solution of KI and $I_2$ having a concentration below a predetermined concentration capable of dissolving Au and very fine abrasive powder not reacting with this aqueous solution were mixed, and the Au thin film was polished using this mixed solution to remove Au on the insulating film (FIG. 18(C)). The etching rate of the solution was set to be below 1,000 Å/min. The abrasive used was silica powder having a minimum grain size of 0.02 μm, and fine cloth such as flannel was used as an abrasive cloth. As a result chemical-mechanical polishing provided gold 73, was buried in the insulating film ($SiO_2$).

FIG. 19 is a micrograph showing the state in which Au on the insulating film was removed by such chemical-mechanical polishing. In FIG. 19, columns of gold buried in a large amount of bias could be seen on the left side, and very thin wires of gold buried in the lines could be seen on the right side. A wiring, the pattern dimension of which was accurately controlled, could be obtained by such a method.

As described above, various methods of the present invention can form the flat gold thin film without involving the growth of needle-like crystals. Since burying in the contact holes and the formation of the flat wiring layer become possible, the present invention greatly contributes to the accomplishment of integrated circuit devices having a higher operational speed. Furthermore, the present invention can obtain a gold thin film having electromigration resistance.

I claim:

1. A method for forming a gold film on a substrate by a chemical vapor deposition, comprising the steps of:

supplying a gold source gas into a reactor;

adjusting a temperature within the range of about 150° to about 240° C. in the reactor at a pressure of at least 10 Torr to attain a kinetically controlled region in the reactor; and depositing a gold film from the gold source gas onto the substrate, the gold film being deposited onto said substrate substantially without forming needle-shape crystals.

2. The method according to claim 1, wherein said gold source gas for forming said gold film is dimethylgold hexafluoroacetylacetonato.

3. A gold film vapor growing method comprising the steps of:

adding, to a starting gas for forming a gold film, a plasma of low energy not completely decomposing said starting gas, producing a partially decomposed starting gas; and supplying said resulting partially decomposed starting gas to a single crystal substrate, forming a single gold film on said single crystal substrate.

4. The gold film vapor growing method according to claim 3, wherein said starting gas for forming said gold film is dimethylgold hexafluoroacetylacetonato.

5. A method for forming first and second gold films on a substrate by chemical vapor deposition, comprising the steps of:

supplying a gold source gas into a reactor;

adjusting a temperature in the reactor at a pressure of at least 10 Torr to attain a kinetically controlled region in the reactor;

depositing the first gold film, from the gold source gas, onto the substrate by a plasma enhanced chemical vapor deposition process, said first gold film being deposited onto said substrate substantially without forming needle-shape crystals;

successively forming said second gold film on said first gold film by an in-situ thermal chemical vapor deposition process.

6. The method according to claim 5, wherein the thickness of said first gold film grown by said plasma enhanced chemical vapor deposition process is smaller than the thickness of said second gold film formed by said in-situ thermal chemical vapor deposition process.

7. The method according to claim 5, wherein said gold source gas for forming said first gold film, and also for forming said second gold film, is dimethylgold hexafluoroacetylacetonato.

8. The method according to claim 1, wherein said steps of adjusting a temperature and depositing a gold film further comprise:

preliminarily heating and decomposing said gold source gas at a pressure within the range of about 10 to about 100 Torr and at a temperature within the range of about 150° to about 240° C., producing an intermediate product; and jetting the resulting intermediate product to said substrate kept in a vacuum of below about $10^{-3}$ Torr so as to form said gold film on said substrate.

9. The method according to claim 8, wherein said gold source gas is dimethylgold hexafluoroacetyl-acetonato.

10. The gold film vapor growing method according to claim 3, wherein said steps of adding a plasma and supplying said resulting partially decomposed starting gas further comprise:

forming an intermediate product by keeping beforehand said starting gas under a pressure state of below about 10 Torr and by generating a plasma at room temperature; and jetting the resulting intermediate product to said substrate kept in a vacuum state of below about $10^{-3}$ Torr so as to form said gold film on said substrate.

11. The gold film vapor growing method according to claim 10, wherein said starting gas is dimethylgold hexafluoroacetyl-acetonato.

12. The gold film vapor growing according to claim 3, wherein said single crystal gold film is substantially free of needle-shape crystals.

13. The method according to claim 1, wherein said steps of adjusting a temperature and depositing a gold film further comprise:

generating a pressure up to 10 Torr on said gold source gas, and adding a plasma generated at room temperature to said pressured gold source gas, producing a partially decomposed intermediate product; and jetting the resulting intermediate product to said substrate kept in a vacuum of below about $10^{-3}$ Torrs so as to form said gold film on said substrate.

14. The method according to claim 1, further comprising the steps of:

mixing an aqueous KI and $I_2$ solution with an abrasive powder which does not react with said solution, producing a polishing agent; and applying said polishing agent to said gold film to remove portions of said gold film from said substrate.

15. The method as claimed in claim 14, wherein said abrasive powder is silica powder having a minimum grain size of 0.02 μm.

* * * * *

UNITED STATES PATENT AND TRADEMARK OFFICE
CERTIFICATE OF CORRECTION

PATENT NO. : 5,491,005
DATED : February 13, 1996
INVENTOR(S) : HOSHINO

It is certified that error appears in the above-indentified patent and that said Letters Patent is hereby corrected as shown below:

Cover Page, Section [56], "OTHER PUBLICATIONS", insert --ANONYMOUS, "Automated System for Thin Film Circuit Repair-Relies on Formation of Micro Plasma to Remove Organic and Subsequent Metal Deposition", Database WPI, Section Ch, Week 9037, Derwent Publications Ltd., London, GB.

Column 2, line 6, change "4A(a), 4A(b) and 4B(a)" to --4A through 4C--.

Column 3, line 66, change "view" to --views--; after "of" insert --a--.

Column 4, line 6, change "A" to --A.--.

Column 7, line 61, after "Fig. 6)." insert hard return and paragraph indentation.

Column 10, line 66, change "Torts" to --Torrs--.

Signed and Sealed this

Twenty-fifth Day of June, 1996

BRUCE LEHMAN

*Attest:*

*Attesting Officer*     *Commissioner of Patents and Trademarks*